(12) United States Patent
Bonde et al.

(10) Patent No.: US 9,907,476 B2
(45) Date of Patent: *Mar. 6, 2018

(54) MULTI-ELECTRODE PERIPHERAL NERVE EVALUATION LEAD AND RELATED SYSTEM AND METHOD OF USE

(71) Applicant: Medtronic Inc., Minneapolis, MN (US)

(72) Inventors: Eric H Bonde, Victoria, MN (US); Eric M Stetz, Coon Rapids, MN (US); Carole A Tronnes, Stillwater, MN (US); James T Henry, Minneapolis, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 24 days.

This patent is subject to a terminal disclaimer.

(21) Appl. No.: 14/543,735

(22) Filed: Nov. 17, 2014

(65) Prior Publication Data

US 2015/0141787 A1    May 21, 2015

Related U.S. Application Data

(62) Division of application No. 11/413,432, filed on Apr. 28, 2006, now Pat. No. 8,892,214.

(51) Int. Cl.
| | | |
|---|---|---|
| *A61N 1/05* | (2006.01) | |
| *A61B 5/04* | (2006.01) | |
| *A61B 5/00* | (2006.01) | |

(52) U.S. Cl.
CPC ........ *A61B 5/04001* (2013.01); *A61B 5/6848* (2013.01); *A61N 1/0551* (2013.01); *A61N 1/0558* (2013.01)

(58) Field of Classification Search
CPC .... A61N 1/0472; A61N 1/048; A61N 1/0488; A61N 1/0551

See application file for complete search history.

(56) References Cited

U.S. PATENT DOCUMENTS

| | | |
|---|---|---|
| 4,010,758 A | 3/1977 | Rockland et al. |
| 4,735,208 A | 4/1988 | Wyler et al. |
| 5,489,294 A | 2/1996 | McVenes et al. |
| 5,653,742 A | 8/1997 | Parker et al. |
| 5,782,892 A | 7/1998 | Castle et al. |

(Continued)

OTHER PUBLICATIONS

Carlton et al., "Canine Evaluation of the InterStim® Tined Anchor: Acute Holding Strength", 2002, 4 pages.

(Continued)

*Primary Examiner* — Eric D. Bertram
(74) *Attorney, Agent, or Firm* — Mueting, Raasch & Gebhardt, P.A.

(57) ABSTRACT

A system for applying an electrical stimulation includes a lead and a stylet slidably disposed within a lumen of the lead body and extending proximally therefrom. The lead includes a plurality of insulated conductor wires electrically isolated from one another and each having a distal segment terminating at distal end, an intermediate segment, and a proximal segment terminating at a proximal end, wherein the distal ends are electrically coupled to a respective one of the stimulating electrodes and the intermediate segments extend proximal the lead body and are characterized as having a non-coiled configuration.

14 Claims, 12 Drawing Sheets

(56) References Cited

U.S. PATENT DOCUMENTS

| | | | |
|---|---|---|---|
| 6,055,456 A | 4/2000 | Gerber | |
| 6,104,960 A | 8/2000 | Duysens et al. | |
| 6,512,958 B1 | 1/2003 | Swoyer et al. | |
| 6,604,283 B1 * | 8/2003 | Kuzma | A61N 1/0541 |
| | | | 228/173.4 |
| 6,847,849 B2 | 1/2005 | Mamo et al. | |
| 6,876,885 B2 | 4/2005 | Swoyer et al. | |
| 6,889,094 B1 | 5/2005 | Kuzma et al. | |
| 6,971,393 B1 | 12/2005 | Mamo et al. | |
| 6,999,819 B2 | 2/2006 | Swoyer et al. | |
| 8,892,214 B2 * | 11/2014 | Bonde | A61N 1/0551 |
| | | | 607/117 |
| 2003/0045919 A1 | 3/2003 | Swoyer et al. | |
| 2003/0120327 A1 | 6/2003 | Tobritzhofer et al. | |
| 2005/0090885 A1 * | 4/2005 | Harris | A61N 1/0553 |
| | | | 607/116 |
| 2006/0089697 A1 * | 4/2006 | Cross, Jr. | A61N 1/056 |
| | | | 607/122 |
| 2006/0190046 A9 | 8/2006 | Gerber | |
| 2006/0190048 A1 | 8/2006 | Gerber | |
| 2006/0195152 A1 | 8/2006 | Gerber | |
| 2007/0050004 A1 | 3/2007 | Swoyer et al. | |

OTHER PUBLICATIONS

"InterStim®—Test Stimulation Components", 2002, Medtronic Instructions Manual, 40 pages.

"InterStim®—Test Stimulation Lead Kit, for use with Model 3625 Test Stimulator", 2002, Medtronic Technical Manual, 28 pages.

\* cited by examiner

MULTI-ELECTRODE PERIPHERAL NERVE EVALUATION LEAD AND RELATED SYSTEM AND METHOD OF USE

This is a division of patent application Ser. No. 11/413,432 filed Apr. 28, 2006, and issued as U.S. Pat. No. 8,892,214 on Nov. 18, 2014, which is incorporated herein by reference.

BACKGROUND OF THE INVENTION

The present invention relates to systems and methods for providing electrical stimulation to bodily tissue, such as electrically stimulating portion of a patient's nervous system. More particularly, it relates to temporarily implantable electrical stimulation leads, such as a peripheral nerve evaluation lead used to stimulate a sacral nerve, and related methods of use.

A number of human bodily functions are affected by the nervous system. For example, bodily disorders, such as urinary incontinence, urinary urge/frequency, urinary retention, pelvic pain, bowel dysfunction (constipation, diarrhea, etc.), erectile dysfunction, etc., are all bodily functions influenced by the sacral nerves. As a point of reference, urinary incontinence is the involuntary loss of control over the bladder. Incontinence is primarily treated through pharmaceuticals and surgery. Many pharmaceuticals do not adequately resolve the issue and can cause unwanted side effects; further, a number of surgical procedures have a low success rate and/or are not reversible. Similar treatment insufficiencies have likewise been noted for many of the other maladies previously mentioned.

As an alternative to conventional pharmaceuticals and/or invasive surgical procedures, neurostimulation has more recently been recognized as a viable treatment approach for many patients. By way of background, the organs involved in bladder, bowel, and sexual function receive much of their control via the second, third, and fourth sacral nerves, commonly referred to as S2, S3, and S4, respectively. Electrical stimulation of these various nerves has been found to offer some control over these functions. Several electrical stimulation techniques have been suggested, including stimulation of nerve bundles within the sacrum. Regardless, in order to consistently deliver electrical stimulation to the sacral nerve(s), certain anatomical obstacles must be addressed. The sacrum is a large, triangular bone situated at the lower part of the vertebral column, and at the upper and back part of the pelvic cavity. The spinal canal runs through the greater part of the sacrum. Further, the sacrum is perforated by the anterior and posterior sacral foramina though which the sacral nerves pass.

With the above anatomical description in mind, partial control over one or more of the functions (or dysfunctions) previously mentioned has been achieved by implanting a neurostimulation lead at or near the sacral nerves. As a point of reference, other nerve(s) or tissue can similarly be electrically stimulated to produce different effects. Relative to sacral nerve stimulation, however, the neurostimulation lead, having several stimulation electrodes, can be permanently implanted within and/or anteriorly beyond the sacral foramen at which the sacral nerve in question is anatomically located. Because the lead, and in particular the stimulation electrodes, must remain in operative proximity to the sacral nerve, the permanent lead (sometimes referred to as a "chronic lead") can be sutured within the patient's body to resist migration. In light of the invasive nature associated with this approach, minimally invasive neurostimulation leads have been developed, incorporating features proximal the electrodes that inhibit migration and/or retrograde dislodgement. Permanent leads of this type are typically somewhat sizable to not only present a sufficient number of electrodes, but to also better resist migration. To promote a minimally invasive implantation technique, the wire conductors associated with the lead electrodes are coiled to from a continuous channel or lumen. Regardless, following initial implant, the coiled wire conductors are collectively contained within a cable extending proximal the electrodes. To complete the implantation procedure, a subcutaneous tunnel is formed within which the cable is located and then coupled to an implantable pulse generator that is otherwise subcutaneously implanted. One example of such a system is available from Medtronic, Inc., of Minneapolis, Minn. under the trade name InterStim®. Other chronic leads/systems are further described in U.S. Pat. Nos. 6,999,819; 6,971,393; and 6,847,849, each commonly assigned to the assignee of the present invention and the teachings of all of which are incorporated herein by reference.

Some patients may view the permanent neurostimulation lead and related pulse generator implantation described above as being a fairly traumatic procedure. Thus, efforts are conventionally made to ascertain in advance whether the patient in question is likely to receive benefit from sacral nerve stimulation. In general terms, the test stimulation procedure entails the temporary implantation of a neurostimulation lead in conjunction with an externally carried pulse generator or other power source. Once in place, the patient is exposed to neurostimulation over a trial period (e.g., 3-7 days) during which the patient can experience the sensation of nerve stimulation during various everyday activities, as well as recording the changes, if any, in the bodily dysfunction of concern (e.g., a patient experiencing urinary incontinence can maintain a voiding diary to record voiding behavior and symptoms with the stimulation). The record of events is then compared with a base line and post-test stimulation diaries to determine the effect, if any, of sacral nerve stimulation on the symptoms being experienced by the patient. If the test stimulation is successful, the patient and his/her clinician can make a better informed decision as to whether permanent implantation and long-term sacral nerve stimulation is a viable therapy option.

Temporary implantation of the neurostimulation lead is normally done in one of two manners. With one approach, sometimes referred to as a "staged implantation," a conventional, permanent or chronic neurostimulation lead is implanted at the desired sacral location, with the cable carrying the coiled conductor wiring being located through a subcutaneous tunnel as described above, and externally extended (or connected to cabling extending) through the patient's skin and coupled to the pulse generator. While viable, this technique entails the use of surgical equipment normally employed to permanently implant the stimulation lead. By way of background, implantation of a permanent sacral nerve stimulation lead normally requires the use of a fairly large introducer (e.g., an elongated, 13 gauge tube), and the chronic stimulation lead has a fairly large diameter. Further, a subcutaneous tunnel is still formed. While local and/or general anesthesia is available, some patients may be apprehensive to participate in a short-term test of this type in view of the size of the instrument(s)/stimulation lead.

To better address the reluctance of some patients to participate in the stimulation test procedure described above, a second technique has been developed that entails the use of a smaller diameter, more simplified neurostimulation lead intended to be implanted on only a temporary basis. In general terms, the temporary stimulation lead (sometimes referred to as a peripheral nerve evaluation lead or "PNE" lead) has a single electrode and is of sufficiently small diameter so as to be percutaneously inserted using a small diameter needle (e.g., a 20 gauge needle). Many patients are not overly threatened by a small diameter needle and thus are more likely to participate in the trial stimulation. The percutaneous test stimulation is similar to an epidural nerve block, except that the temporary lead is inserted and left in the patient's back during the trial. The end of the lead that remains on the outside of the patient's body is secured to the patient's skin with, for example, surgical tape. Upon conclusion of the trial stimulation, the lead is removed from the patient.

While generally preferred by patients, the percutaneous, PNE lead technique may have certain drawbacks. For example, while the temporary simulation lead is highly capable of delivering the necessary stimulation energy throughout the evaluation period, it is possible that the lead may migrate. For example, any pulling or tugging on the proximal end of the lead body (from outside of the patient's body) could be directly communicated to the lead's electrode, thus creating a higher likelihood of electrode dislodgement and poor stimulation. Efforts have been made to address this concern, for example as described in U.S. Pat. No. 6,104,960, the teachings of which are incorporated herein by reference and assigned to the assignee of the present invention. In particular, a temporary neurostimulation lead is described as having a coiled configuration that better accommodates axial forces placed onto the lead body (e.g., tugging or pulling on the proximal end of the lead body). However, conventional PNE-type leads are unipolar, requiring a ground or return pad being secured to the patient's skin. The ground pad may become displaced during the patient's daily activities and/or lose electrical connection, rendering the test procedure of little value. Further, while current PNE leads are better able to resist migration, accidental dislodgement is likely more prevalent that otherwise observed with a chronic lead.

In light of the above, a need exists for a medical electrical lead which may be safely and effectively temporarily implanted in a minimally invasive manner, but which better inhibits axial migration of dislodgement of the lead body from the stimulation site, such as a sacral location, and provides bipolar operation.

SUMMARY OF THE INVENTION

Some aspects in accordance with principles of the present invention related to an implantable medical electrical lead for applying an electrical stimulation energy to bodily tissue of a patient, such as a portion of the patient's nervous system, from a power source located external the patient. The lead is generally defined by a distal section, an intermediate section and a proximal section. With this in mind, the lead includes a lead body, a plurality of insulated conductor wires, and a plurality of connector elements. The lead body is provided at the distal section of the lead and includes a plurality of stimulating electrodes arranged in an electrode array and at least one anchoring device. In some embodiments, the anchoring device can be located, for example, proximal the electrode array. The insulated wires are electrically isolated from one another, each having or defining a distal segment, an intermediate segment, and a proximal segment. The distal segment terminates in a distal end that is electrically coupled to a respective one of the stimulating electrodes. The intermediate segment extends proximal the lead body in defining the intermediate section of the lead, and is characterized as having a non-coiled configuration. The plurality of connector elements are formed in a connector array at the proximal section of the lead. Individual ones of the connector elements are electrically coupled to the proximal segment of a respective one of the insulated wires, and facilitate electrical coupling to an external power source. With this configuration, the intermediate segments of the insulated wires are extendible through a patient's skin and are sealable relative to a surface of the patient's skin. In some embodiments, the lead is adapted for providing temporary electrical stimulation to a sacral nerve, with the lead operating in a bipolar mode and the anchoring device serving to inhibit migration of the stimulating electrodes. In other embodiments, the distal segment of each of the insulated wires forms a coiled wire lead conductor disposed within the lead body. In yet other embodiments, the lead body includes a plurality of coiled wire lead conductors that electrically connect individual ones of the stimulating electrodes to respective ones of the insulated wires.

Yet other aspect in accordance with principles of the present invention relate to a system for applying electrical stimulation to bodily tissue of a patient from a power source located external the patient. The system includes a lead and a stylet. The lead is generally defined by a distal section, an intermediate section and a proximal section. With this in mind, the lead includes a lead body, a plurality of insulated conductor wires, and a plurality of connector elements. The lead body forms a lumen and includes a plurality of stimulating electrodes arranged in an electrode array and at least one anchoring device. The anchoring device can be located proximal the electrode array. The insulated wires are electrically isolated from one another, each having or defining a distal segment, an intermediate segment, and a proximal segment. The distal segment terminates in a distal end that is electrically coupled to a respective one of the stimulating electrodes. The intermediate segment extends proximal the lead body in defining the intermediate section of the lead, and is characterized as having a non-coiled configuration. The plurality of connector elements are formed in a connector array at the proximal section of the lead. Individual ones of the connector elements are electrically coupled to the proximal segment of a respective one of the insulated wires, and facilitate electrical coupling to an external power source. The stylet is sized to be slidably disposed within the lead body lumen to facilitate temporary implantation of the lead body. In some embodiments, the intermediate segments of the insulated wires are free of the stylet upon final assembly; in other embodiments the intermediate segments of the insulated wires are temporarily wrapped about the stylet. In yet other embodiments, the stylet is a directional guide wire adapted to serve as an electrical probe.

Yet other aspects in accordance with principles of the present invention relate to a method of providing electrical stimulation to bodily tissue of a patient at a stimulation site via a power source located external the patient. The method includes providing an implantable medical lead generally defined by a distal section, an intermediate section and a proximal section. The lead includes a lead body, a plurality of insulated conductor wires, and a plurality of connector elements. The lead body is provided at the distal section of the lead and includes a plurality of stimulating electrodes arranged in an electrode array and at least one anchoring device. The insulated wires are electrically isolated from one another, each having or defining a distal segment, an intermediate segment, and a proximal segment. The distal segment terminates in a distal end that is electrically coupled to a respective one of the stimulating electrodes. The intermediate segment extends proximal the lead body and is characterized as having a non-coiled configuration. The plurality of connector elements are formed in a connector array at the proximal section of the lead. Individual ones of the connector elements are electrically coupled to the proximal segment of a respective one of the insulated wires. The lead body is percutaneously delivered to the stimulation site through an incision in the patient's skin. Each of the insulated wires are extended through the incision such that a first region of each of the insulated wires is beneath the patient's skin and a second region of each of the insulated wires extends outwardly from the patient's skin. At least a portion of a perimeter of each of the insulated wires is sealed to the patient's skin (preferably in a manner that prevents infection). Finally, the plurality of connector elements are electrically coupled to a power source located external the patient. In some embodiments, the method is performed as part of a sacral nerve stimulation procedure, and is characterized by the absence of forming a subcutaneous tunnel.

Yet other aspects in accordance with principles of the present invention relate to a temporarily implantable medical electrical lead for non-direct contact electrical stimulation of a sacral nerve. The lead is generally defined by a distal section, an intermediate section and a proximal section. With this in mind, the lead includes a lead body, a plurality of insulated conductor wires, and a plurality of connector elements. The lead body is provided at the distal section of the lead and includes a plurality of stimulating electrodes arranged in an electrode array and at least one anchoring device. The anchoring device can be located proximal the electrode array. The insulated wires are electrically isolated from one another, each having or defining a distal segment, an intermediate segment, and a proximal segment. The distal segment terminates in a distal end that is electrically coupled to a respective one of the stimulating electrodes. The intermediate segment extends proximal the lead body in defining the intermediate section of the lead, and is characterized as having a non-coiled configuration. The plurality of connector elements are formed in a connector array at the proximal section of the lead. Individual ones of the connector elements are electrically coupled to the proximal segment of a respective one of the insulated wires, and facilitate electrical coupling to an external power source. With this configuration, the intermediate segments of the insulated wires are extendible through a patient's skin and are sealable relative to a surface of the patient's skin. Further, the lead body is capable of being inserted through a foramen of the sacrum to position at least one of the stimulating electrodes into operative relation with a sacral nerve to provide stimulation to the sacral nerve.

DETAILED DESCRIPTION OF THE INVENTION

Figure 1:
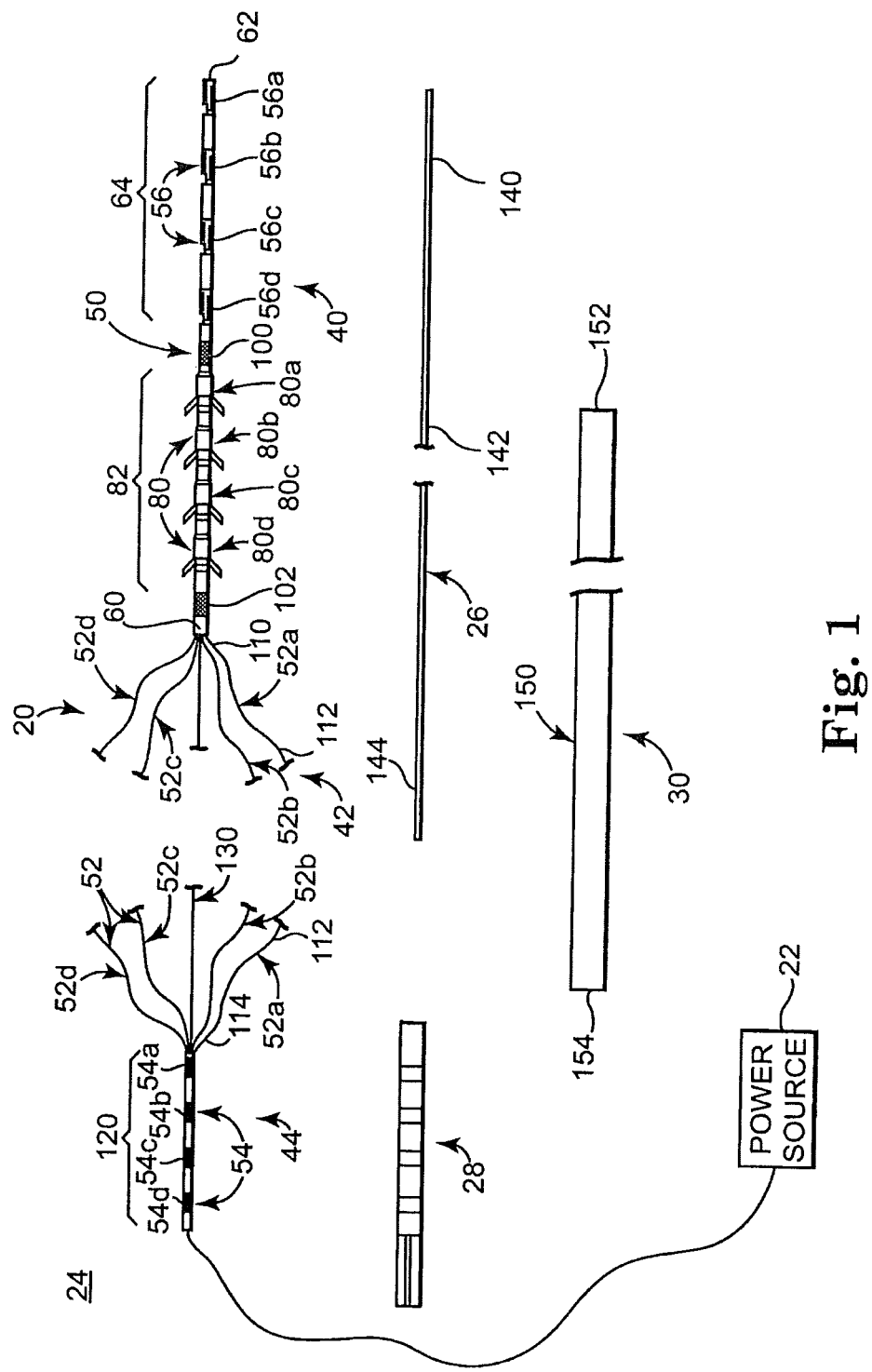
FIG. 1 is a simplified plan view of a system for providing electrical stimulation to bodily tissue of a patient, including an implantable medical electrical lead in accordance with principles of the present invention.

One embodiment of a temporarily implantable lead 20 in accordance with principles of the present invention for providing electrical stimulation to bodily tissue of a patient from an external power source 22, such as part of a peripheral sacral nerve stimulation evaluation, is shown in FIG. 1 as part of a system 24. The system 24 can includes components apart from those shown (and the power source may or may not be considered part of the system 24), but generally includes the lead 20, a stylet 26, a connector assembly 28, and an introducer 30. Details on the various components are provided below. In general terms, however, the lead 20 is akin to a permanent or chronic lead, but can be temporarily implanted in a relative non-traumatic fashion (e.g., does not require subcutaneous tunneling) with use of, in some embodiments, the stylet 26 (that can be a conventional stylet or a direction guide wire) and the introducer 30. Once implanted at a stimulation site, the lead 20 is electrically coupled to the power source 22, via the connector assembly 28, which in turn causes electrical energy to be applied to the lead 20 and thus the stimulation site.

The lead 20 can assume a variety of forms differing from the one configuration shown in FIG. 1, and generally defines a distal section 40, an intermediate section 42, and a proximal section 44. With these designations in mind, the lead 20 includes a lead body 50, a plurality of insulated wires 52 (referenced generally), and a plurality of connector elements 54 (referenced generally). The lead body 50 is provided at the distal section 40 of the lead 20, and includes a plurality of stimulating electrodes 56. Respective ones of the electrodes 56 are electrically coupled to respective ones of the insulated wires 52. The wires 52 extend proximally from the lead body 20 to define the intermediate section 42, and electrically connect the electrodes 56 to respective ones of the connector elements 54. Finally, the connector elements 54 are adapted for mounting to the connector assembly 28 and for electrical coupling to the power source 22.

In some embodiments, the lead body 50 has a general construction similar to the leads described in U.S. Pat. No. 6,999,819, the teachings of which are incorporated herein by reference, extending between a proximal end 60 and a distal end 62. With additional reference to FIG. 2, the lead body 50 includes at least two, preferably at least three, even more preferably four (or more) of the electrodes (identified in FIGS. 1 and 2 as 56a, 56b, 56c, and 56d), provided as ring-shaped electrodes and arranged in an electrode array 64 extending proximally from the distal end 62. A diameter of the lead body 50 is, in one embodiment, in the range of about 0.5 mm to about 2 mm, and the electrode array 64 extends proximally longitudinally for a length of about 25 mm from the distal end 62. Other dimensions are also acceptable. In one embodiment, the electrodes 56a-56d are made of a solid surface, bio-compatible material, e.g., a tube formed of platinum, platinum-iridium alloy, stainless steel, etc., of about 3 mm in length (although other lengths, either greater or lesser, are also equally acceptable) that does not degrade in the presence of electrical stimulation energy. With specific reference to FIG. 2, adjacent pairs of the electrodes 56a-56d are separated and electrically isolated from one another by an insulator band 66 formed of an electrically non-conductive material. For example, the insulator bands 66 can be formed by a length of non-conductive tubing or sheath 68 that otherwise carries the electrodes 56a-56d.

Each of the stimulation electrodes 56a-56d is electrically coupled to the distal end of a corresponding coiled wire lead conductor (not shown) disposed within an interior of the lead body 50. Thus, with the one embodiment of FIGS. 1 and 2, four of the interior, coiled wire lead conductors are provided. The coiled wire lead conductors are, in one embodiment, provided as the distal segment of the respective wires 52 as described below; alternatively, the interior coiled wire lead conductors are provided apart from, and subsequently electrically connected to respective ones of the wires 52. Regardless, the coiled wire lead conductors (e.g., the coiled distal segments of the wires 52) terminate at or adjacent the proximal end 60 of the lead body 50. The coiled wire lead conductors are formed of conductive metal (e.g., stainless steel such as 316L multi filament wire, MP35N allow, etc.) and are separated isolated from one another by an insulative coating. Further, the coiled wire lead conductors are wound, with the one embodiment of FIGS. 1 and 2 in which four of the coiled wire lead conductors are provided, in a quadra-filar manner having a common winding diameter within the lead body 50 (e.g., within the outer sheath 68). The coil formed by the coiled wire lead conductors defines a lumen (referenced generally at 70 in FIG. 2) of the lead body 50. It will be understood, however, that a further inner tubular sheath could be interposed within the aligned wire coils to provide the lead body lumen.

In addition to the electrodes 56a-56d and inner coiled wire lead conductors, the lead body 50 includes at least one, preferably a plurality, of anchoring devices 80 (referenced generally), such as the anchoring devices 80a-80d combining to define an anchoring device array 82. The anchoring device(s) 80 is formed on the lead body 50, proximal the electrode array 64, that is otherwise adapted to be implanted in and engage subcutaneous tissue to inhibit axial movement of the lead body 50 and dislodgment of the stimulation electrodes 56a-56d. The anchoring device(s) 80 can assume a variety of forms capable of providing some degree of fixation within a patient, and in one embodiment, is a tine assembly.

In the one embodiment shown, four of the anchoring devices 80a-80d are provided, although any other number, either greater or lesser, is equally acceptable. Further, while the anchoring devices 80a-80d are illustrated as being substantially identical, in other embodiments, one or more of the anchoring device(s) 80a-80d can have an entirely different configuration. With the one embodiment in which the anchoring devices 80a-80d are tine assemblies, and with specific reference to FIG. 2, each assembly 80a-80d includes at least one, preferably more than one, flexible, pliant tine 84 (referenced for the tine assembly 80a). Each tine 84 has a tine width and thickness, and extends through a tine length from an attached end 86 to a free end 88. The attached end 86 is attached to the lead body 50 structure (e.g., the outer sheath 68) from a tine attachment site and supports the tine 84 extending outwardly of the lead body 50 and proximally toward the proximal end 60. The tines 84 are adapted to be folded inward against the lead body 50 structure when fitted into and constrained by the lumen of the introducer 30 (FIG. 1) such that the tine free ends 88 are urged toward or alongside the attached end 86 of an adjacent, proximal tine assembly 80b-80d (e.g., the free ends 88 of the tines 84 of the first tine assembly 80a are urged toward the attached ends 86 of the second tine assembly 80b). A longitudinal spacing between the tine assemblies 80a-80d is such that in the folded state, the tine assemblies 80a-80d do not overlap one another. In further embodiments, one of all of the tine assemblies 80a-80d exhibit a shape memory attribute (e.g., formed of a biocompatible plastic such as medical grade silicone rubber or polyurethane, superelastic alloy material, etc.), such that upon removal of an external force otherwise causing the tine(s) 84 to fold (e.g., upon removal of the lead body 50 from a tubular member such as the introducer 30), the tines 84 will automatically revert (or self-revert) to the radially outwardly extensions shown in FIG. 2. Various acceptable configurations of the tine assemblies 80a-80d are described in greater in U.S. Pat. No. 6,999,819. Once again, however, the anchoring device(s) 80 can assume a variety of other forms that may or may not constitute a tine assembly.

In some embodiments, the lead body 50 can further include visual and radiographic imaging bands 100, 102. The bands 100, 102 can be formed of materials known in the art for promoting visualization in confined bodily areas of a patient, and can be carried by or assembled to the tubing 68, for example. In this regard, in one embodiment, the bands 100, 102 are located distal to and proximal to, respectively, the anchoring device array 82 to provide a clinician with information indicative of a location of the anchoring device array 82 within the introducer 30 and as the introducer 30 is withdrawn to expose the anchoring device array 82 as described below. In other embodiments, one or both of the bands 100, 102 can be positioned at other locations along a length of the lead body 50, and/or more than two of the visual and radiographic imaging bands 100, 102 can be provided. In yet other alternative embodiments, one or both of the bands 100 and/or 102 can be eliminated.

Figure 2:
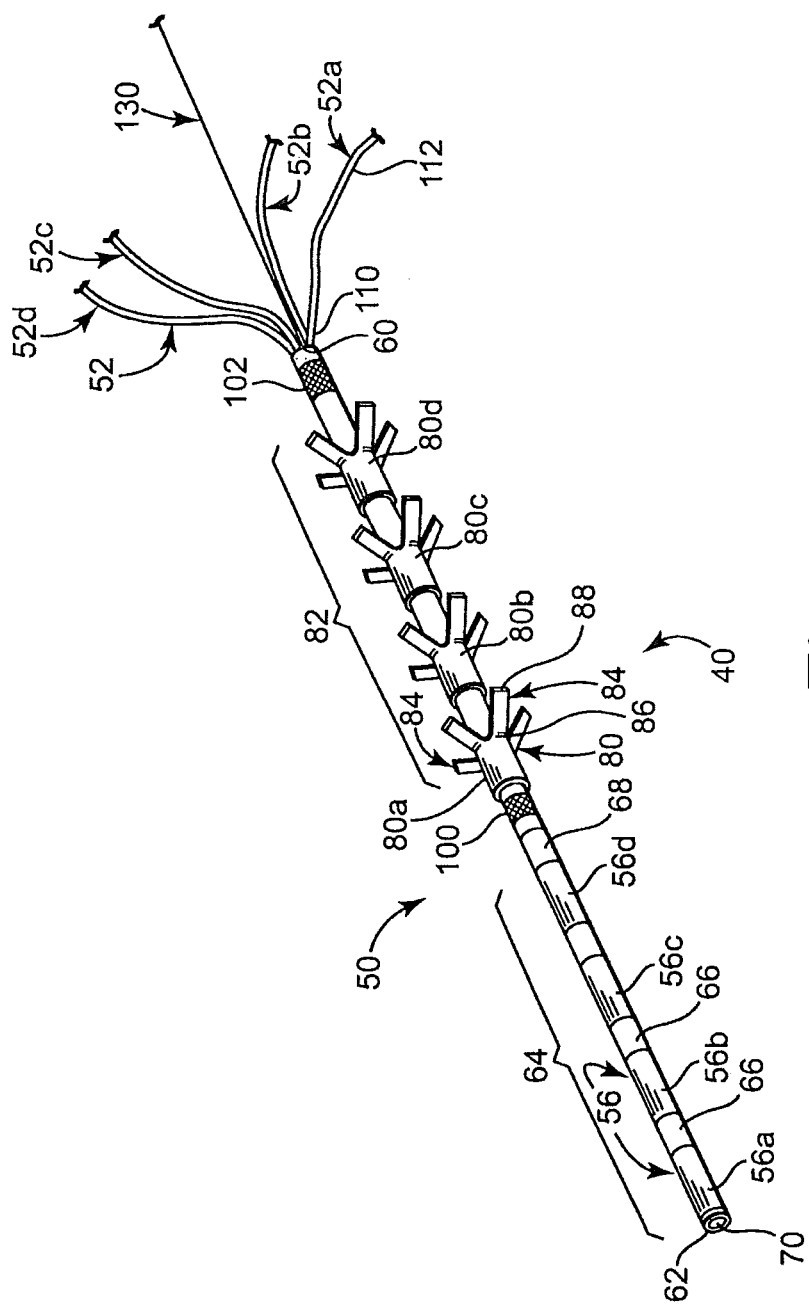
FIG. 2 is an enlarged, perspective view of a portion of the lead of FIG. 1.

With continued reference to FIGS. 1 and 2, each of the insulated wires 52 includes or defines a distal segment 110 (referenced for one of the insulated wires 52 in each of FIGS. 1 and 2) terminating at a distal end (hidden within the lead body 50 in the view of FIGS. 1 and 2), an intermediate segment 112, and a proximal segment 114 (FIG. 1) terminating at a proximal end (referenced generally in FIG. 1). As described above, the insulated wires 52, and in particular the intermediate segments 112 thereof, extend proximally from the proximal end 60 of the lead body 50; with these designations in mind, then, the intermediate segments 112 combine to define the intermediate section 42 of the lead 20. The distal segments 110/distal ends are electrically coupled to respective ones of the coiled wire lead conductors (not shown) otherwise electrically connected to the electrode array 64. In this regard, individual ones of the wires 52 can be formed as integral extensions of respective one of the coiled wire lead conductors; alternatively, the insulated wires 52 can be formed apart from the coiled wire lead conductors and subsequently electrically connected to respective ones of the coiled wire lead conductors. In any event, the insulated wires 52 correspond in number to the number of stimulating electrodes 56 provided with the lead body 50. Thus, with respect to the one embodiment of FIGS. 1 and 2, the plurality of insulated wires 52 includes first, second, third, and fourth insulated wires 52a-52d, it being understood that any other number, either greater or lesser, is equally acceptable.

The insulated wires 52 each include an electrically conductive wire core (e.g., stainless steel such as 316L multi filament wire; MP35N alloy; etc.) surrounded by an electrically non-conductive material such as polyurethane, fluoropolymer, silicone rubber, PTFE, ETFE, polyester, etc., that is amenable to being surgically sealed to a patient's skin, as described below. With this construction, the individual ones of the wires 52 are electrically isolated from one another in proximal extension from the lead body 50. For example, with the one embodiment of FIG. 1, the first insulated wire 52a is electrically isolated from the second, third and fourth insulated wires 52b-52d; etc. While the insulated wires 52 can be formed of materials identical to those associated with the coiled wire lead conductors (and, in fact, can be homogenously formed with the coiled wire lead conductors), in terms of physical configuration, the insulated wires 52 differ from the coiled wire lead conductors. In particular, the insulated wires 52 are characterized as having a non-coiled configuration. As such, the insulated wires 52 can be "straight" insulated wires, with a certain level of flexibility permitting bending or curving of each of the insulated wires 52 to any spatial orientation desired by a clinician without causing a break in electrical conductivity. This non-coiled attribute can be further characterized as the insulated wires 52 not individually defining or forming an internal or central passage or lumen along at least the intermediate section 42 (e.g., the first insulated wire 52a does not define or form a central lumen along at least the intermediate section 42, etc.), in contrast to a configuration of the coiled wire lead conductors.

In one embodiment, the insulated wires 52 are not permanently exteriorly encompassed by a separate body along at least the intermediate section 42. That is to say, the lead 20 does not, in accordance with one embodiment, include a separate tubing enclosing the insulated wires 52 in the form of conventional cabling. It will be understood that the insulated wires 52 may be temporarily inserted within a separate tubular body (e.g., the introducer 30) as part of a particular procedure; however, the lead 20 itself is configured to render the insulated wires 52 free to move relative to one another along the intermediate section 42. Thus, relative to the intermediate section 42, the insulated wires 52 can be easily moved and positioned to a desired spatial orientation by a user, such as a clinician. In other embodiments, however, the lead 20 can include additional tubing otherwise encasing the insulated wires 52 along the intermediate section 42. Further, the insulated wires 52 can be exteriorly connected to one another along the proximal section 44 (e.g., the insulated wires 52 can be twisted together as a group along the respective proximal segments 114), and/or can be temporarily associated with one another along the intermediate section 42 (such as by braiding about the stylet 26 as described below) in other embodiments.

As shown in FIG. 1, the proximal segment 114 of each of the insulated wires 52 extends to or along the proximal section 44 of the lead 20, and terminates at (or is electrically coupled to) a respective one of the electrical connector elements 54 (referenced generally). Thus, with the one embodiment of FIG. 1, the lead 20 includes four of the connector elements 54a-54d arranged in a connector element array 120. The connector elements 54a-54d are each adapted to be electrically coupled to the power source 22 (e.g., a pulse generator). Further, the connector element array 120 is, in one embodiment, carried by the connector assembly 28 to facilitate ease of electrical coupling to the power source 22. Alternatively, the connector elements 54 can be proved apart from the connector assembly 28.

With the above construction, the lead 20 permits delivery of electrical stimulation energy from the power source 22 to one or more of the stimulating electrodes 56 upon electrically coupling the connector elements 54 to the power source 22. In particular, energy from the power source 22 is conducted through one or more of the insulated wires 52 (via the corresponding connector element 54) to the corresponding coiled wire lead conductor (not shown) otherwise electrically connected to (or formed by) the wire 52 through which energy is being conducted. This coiled wire lead conductor(s), in turn, conducts the electrical energy to the corresponding stimulating electrode 56. To this end, the lead 20 can be operated in a bipolar stimulation mode; however, the lead 20 can also be operated in a unipolar stimulation mode.

As described below, the lead 20, and in particular the lead body 50, can be temporarily implanted in a variety of fashions. Following implantation, a clinician may desire the ability to remove the lead body 50 from the implantation/stimulation site by applying a pulling force onto the proximal section 44 of the lead 20. With this in mind, in one embodiment, the lead 20 can further include a tether 130. The tether 130 can assume a variety of forms, and is preferably a thin, surgically compatible strand (e.g., a surgical suture, flexible insulated wire, etc.) extending from the proximal section 44 to the distal end 62 of the lead body 50. In this regard, in one embodiment the tether 130 is disposed within an interior of the lead body 50 and extends apart from the connector assembly 28, although in other embodiments, the tether 130 can be secured to the connector assembly 28. Regardless, the tether 130 provides a means for applying a pulling force on to the lead body 50 from a location external the patient in a manner that does not otherwise impart a strain force directly on to the insulated wires 52 (that might otherwise negatively affect a conductivity of the insulated wires 52). In other embodiments, however, the tether 130 can be eliminated.

The stylet 26 can assume a variety of forms and defines a distal portion 140, an intermediate portion 142, and a proximal portion 144. In one embodiment, the stylet 26 has a uniform diameter, with the distal portion 140 being sized to be slidably received within the lumen (not shown) of the lead body 50. The proximal portion 144 is adapted to be coupled to the connector assembly 28 in some embodiments as described below. With the one embodiment of FIG. 1, the stylet 26 is akin to a stylet conventionally used to implant a permanent neurostimulating lead, such as a lead stylet provided with an InterStim® stimulation lead package (Product Number 3093) available from Medtronic, Inc. of Minneapolis, Minn., with the stylet 26 being adapted to partially stiffening the lead body 50 to facilitate implantation. In other embodiments described below, the stylet 26 is akin to a directional guide wire that may or may not provide electrical probing features.

Similarly, the connector assembly 28 can assume a variety of forms, and is generally configured to maintain the connector element array 122 for coupling to the power source 22. In some embodiments, the connector assembly 28 is further adapted for maintaining the stylet 26 during a particular implantation procedure, and in particular selectively coupling the stylet to the introducer 30. Thus, the connector assembly 28 can have a configuration compatible with a configuration of the introducer 30. In some embodiments, the connector assembly 28 is akin to lead connector assemblies provided with an InterStim® lead package (Product Number 3093) available from Medtronic, Inc. of Minneapolis, Minn.

The introducer 30 can also assume a variety of forms, and can be provided with other components not shown as part of an introducer assembly. In general terms, however, the introducer 30 is or includes a tubular member or sheath 150 having distal end 152, a proximal end 154, and a lumen (not shown) sized to slidably receive the lead body 50, and is configured to facilitate percutaneous implantation of the lead body 50. To this end, the introducer 30 can be a continuous, or can include portions that are separable from one another, for example a splittable introducer available with an InterStim® introducer assembly (Product Number 355018) available from Medtronic, Inc. of Minneapolis, Minn. Alternatively, however, the introducer 30 can have other conventional configurations. Even further, in other embodiments described below, the introducer 30 can be eliminated.

Figure 3A:
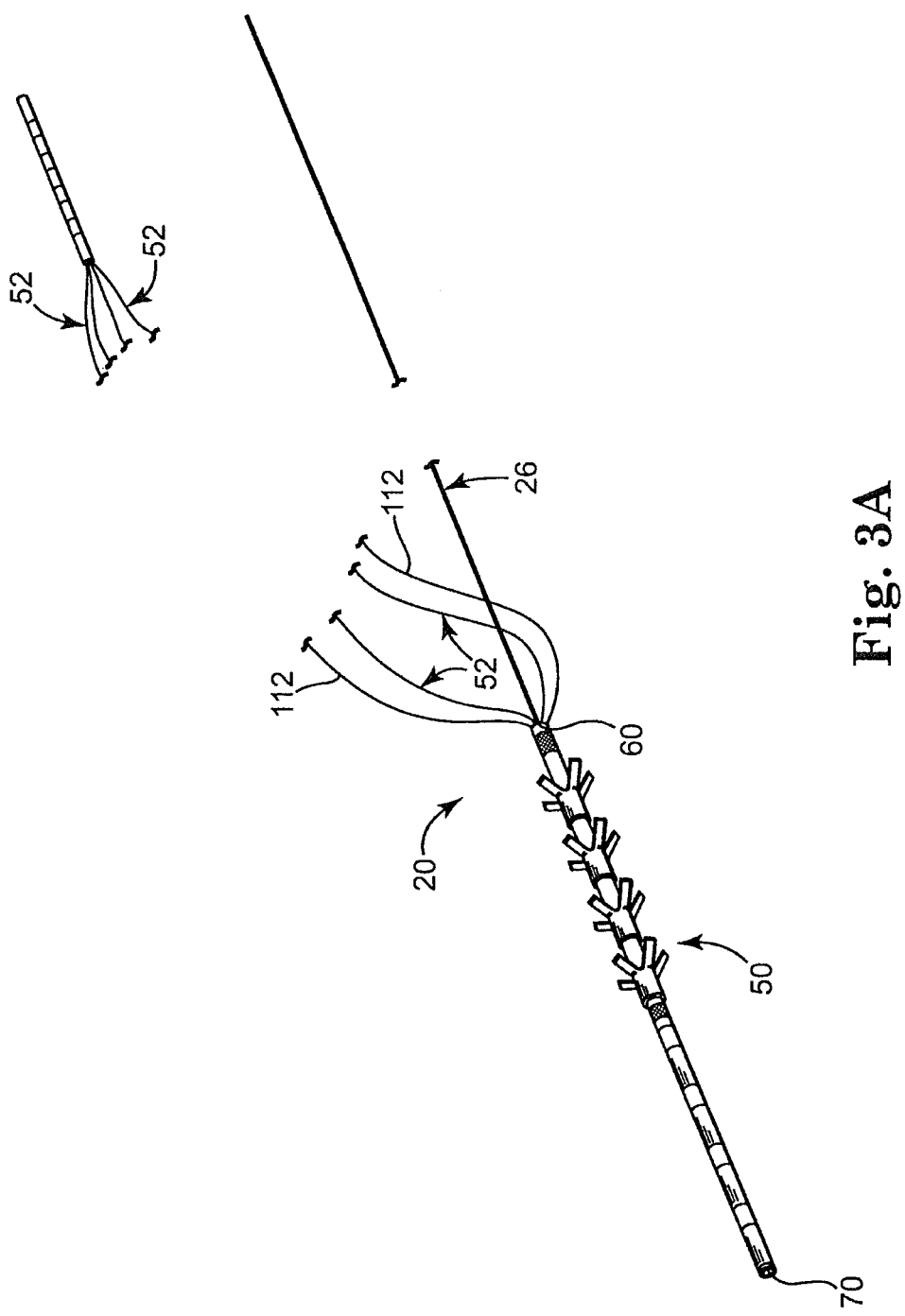
FIG. 3A is a simplified, perspective view of a portion of the system of FIG. 1, illustrating assembly of the lead to a stylet.
Figure 3B:
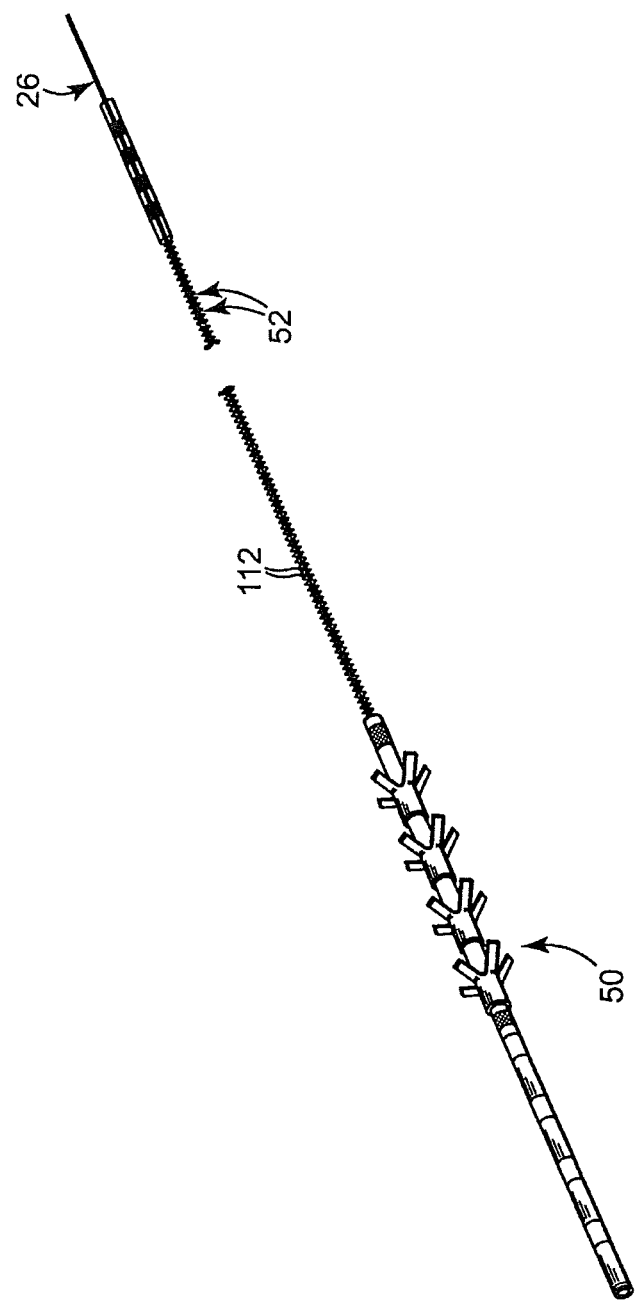
FIG. 3B is an alternative embodiment of the assembly of FIG. 3A.

Partial assembly of the system 24, and in particular the lead 20 and the stylet 26 is shown in FIG. 3A (for purposes of explanation, the tether 130 (FIG. 1) is omitted from the view of FIG. 3A). The stylet 26 is shown as being slidably disposed with the lumen 70 of the lead body 50, and extending proximally therefrom. The insulated wires 52 also extend proximally from the proximal end 60 of the lead body 50. In this regard, at least along the intermediate segments 112 thereof, the insulated wires 52 are free from the stylet 26. In an alternative embodiment illustrated in FIG. 3B (that again does not otherwise show the tether 130), the insulated wires 52 are temporarily connected to the stylet 26, and in particular are braided about the stylet 26. Regardless, at least upon removal of the stylet 26 as part of an implantation procedure, the wires 52 can be freely moved, curved, flexed, etc., relative to one another and/or as a collective grouping along the intermediate segments 112.

Figure 4A:
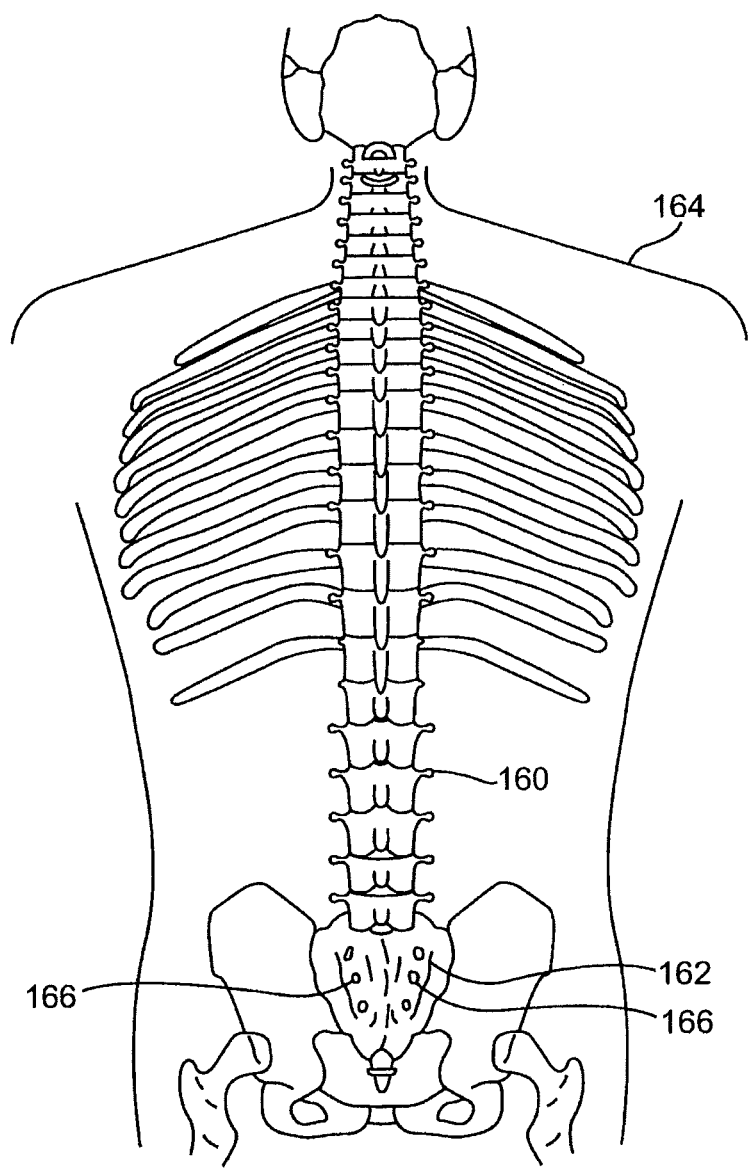
FIG. 4A is a posterior view of a spinal column of a patient, showing a location of a sacrum relative to an outline of the patient's body.
Figure 4B:
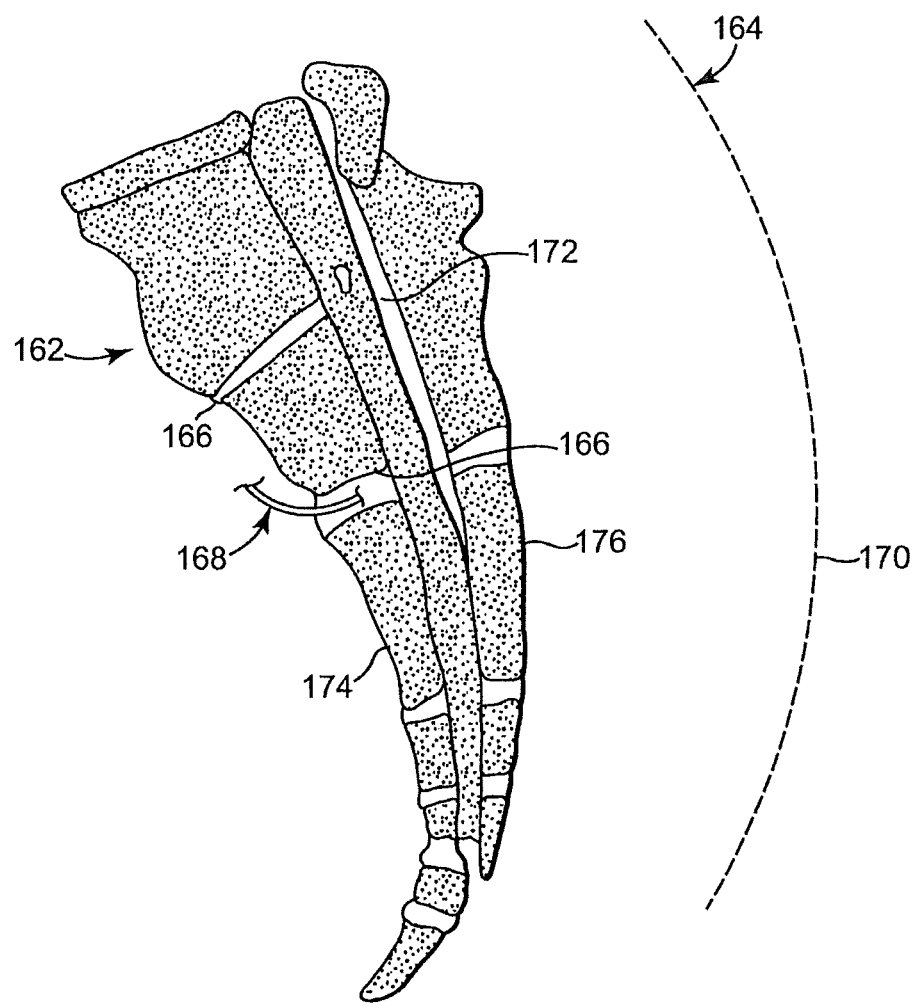
FIG. 4B is a simplified sectional view of a human anatomy in a region of the sacrum.

Returning to FIG. 1, the system 24 in accordance with principles of the present invention can be utilized to provide temporary medical electrical stimulation to a wide variety of bodily structures via a percutaneous approach in conjunction with the external power source 22. For example, the system 24 can be deployed to stimulate one or more nerves of the nervous system. Alternatively, the system 24 can be used in other applications requiring electrical stimulation, such as procedures to rehabilitate muscle dysfunction by neuromodulation (e.g., functional electrical stimulation) of muscular behavior. In one embodiment, however, the system 24 is employed to provide electrical stimulation to a sacral nerve(s), for example as part of a peripheral sacral nerve simulation test or evaluation. With respect to this one exemplary application, FIG. 4A provides a posterior view of a spinal column 160 showing a location of a sacrum 162 relative to an outline of a patient's body 164. As shown, the sacrum 162 has a series of holes or foramen 166 therethrough. Each foramen 166 provides access to sacral ventral nerves (not shown). This relationship is further illustrated in FIG. 4B whereby sacral nerves (a peripheral sacral nerve of which is illustrated schematically and generally referenced at 168) extend along the sacrum 162, generally opposite a dorsal skin surface 170 of the patient's body 164, and through or from a sacral canal 172. FIG. 4B further illustrates a pelvic surface 174 and a dorsal surface 176 of the sacrum 162.

Figure 5:
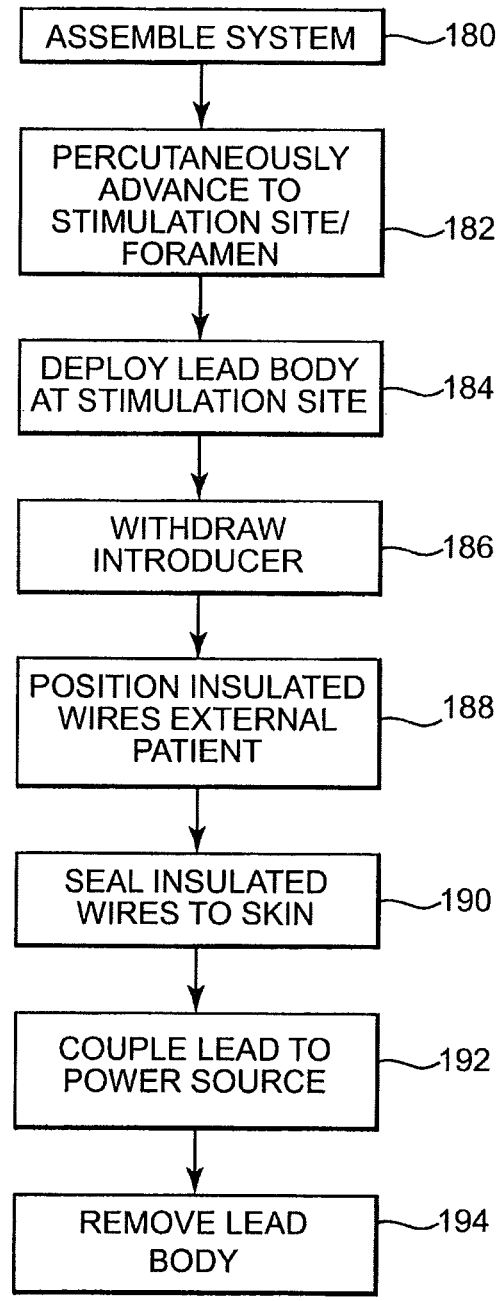
FIG. 5 is a flow diagram relating to a method of delivering an electrical stimulation to a portion of a patient's nervous system.

With the above anatomical description in mind, one method using the system 24 to provide medical electrical stimulation to at least one of the sacral nerves 168 in accordance with principles of the present invention is provided by the flow diagram of FIG. 5, in conjunction with the views of FIGS. 1 and 6A-6D. The system 24 is assembled at step 180 such that the distal section 40 of the lead 20 (and in particular the lead body 50 including the electrode array 64 and the anchoring device array 82) is disposed within the lumen (not shown) of the introducer 30. The stylet 26 is assembled to the lead 20 as previously described (e.g., FIG. 3A or 3B), the distal portion 140 being slidably disposed with the lumen 70 (FIG. 2) of the lead body 50 so that a distal tip of the stylet 26 closes a distal end of the lead body lumen.

Figure 6A:
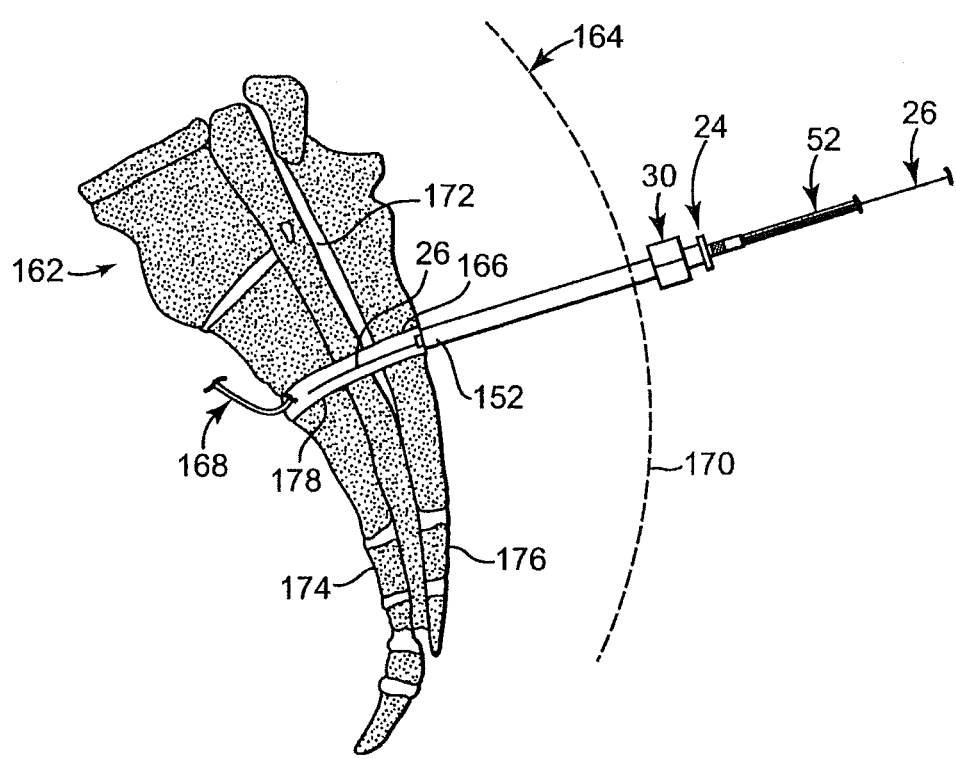
FIGS. 6A-6D illustrate delivery of a stimulation lead to a sacrum of a patient in accordance with principles of the present invention.

The so-assembled system 24 is percutaneously advanced toward a stimulation site (referenced generally at 178 in FIGS. 6A-6D) at step 182 and in particular the distal end 152 of the introducer 30 is advanced toward the selected foramen 166 as shown in FIG. 6A. In this regard, and in accordance with one embodiment, to determine the best location for the stimulating electrodes 56 (FIG. 1), and insulated foramen needle (not shown) with both ends exposed for electrical stimulation can be used to locate the foramen 166 and locate the sacral nerve 168 by applying electrical stimulation to the needle using an external pulse generator. The efficacy of the location is tested by evaluating the physiologic response in relation to threshold energy required to elicit the response. As a point of reference, for control of incontinence, the clinician preferably implants the lead body 50 (FIG. 1) near the S3 sacral nerves. The lead body 50 may, however, be inserted near any of the sacral nerves 168 including the S1, S2, S3, or S4 sacral nerves accessed via the corresponding foramen 166 depending upon the necessary or desired physiologic response.

The advancement of the introducer 30 can be accomplished separately over a guide wire (not shown) previously percutaneously advanced from the skin incision into the foramen 166 to establish the angle of advancement. Also, the introducer 30 can be a two-part or splittable introducer having an inner introducer element that may be first advanced toward the stimulation site 178 by itself or over a previously introduced guide wire (not shown), and an outer introducer that can be introduced over the inner element to dilate the tissue, whereupon the inner element is removed. Any percutaneous introduction tools and techniques can be employed that ultimately provides the introducer 30 at the location depicted in FIG. 6A. As a further point of reference, the system 24 can be fully assembled after the distal end 152 of the introducer 30 is positioned at or adjacent the selected foramen 166; in other words, step 180 can occur after step 182.

Figure 6B:
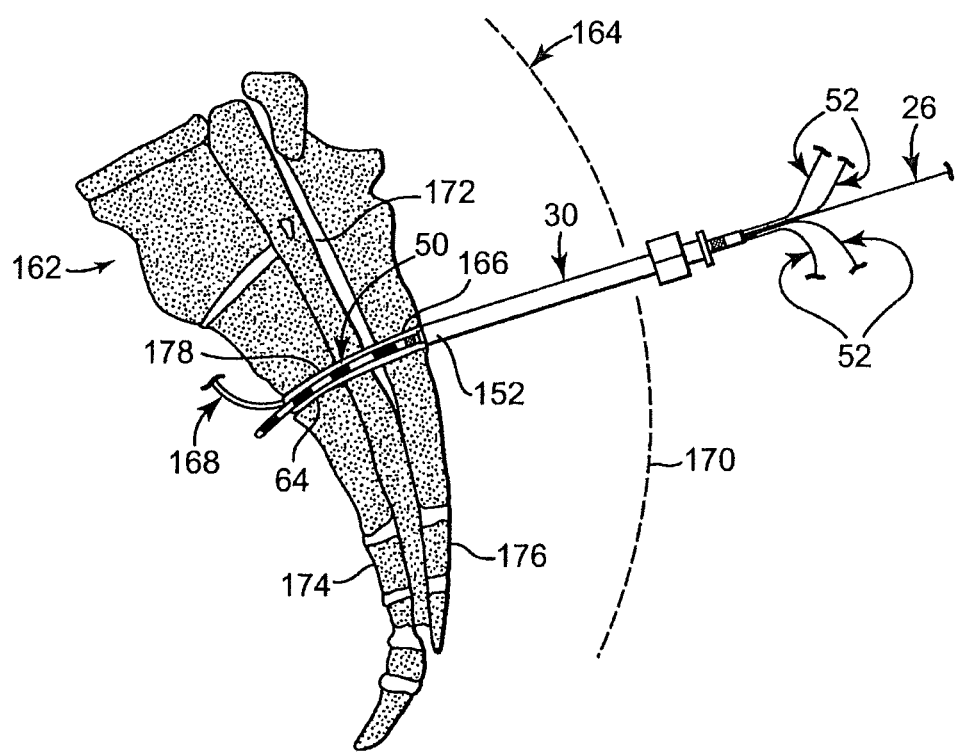

The lead body 50 (hidden in FIG. 6A) is at least partially deployed from the introducer 30 at step 184. To this end, the stylet 26 can first be advanced distally or anteriorly through the foramen 166 as shown in FIG. 6A, or the lead body 50 and the stylet 26 can both be advanced distally out of the distal end 152 of the introducer 30/introducer lumen (not shown) to advance the stimulation electrode array 64 into or through the foramen 166 from the posterior entrance into casual contact with the sacral nerve 168 as depicted in FIG. 6B. As a point of reference, FIG. 6B depicts the insulated wires 52 as extending in a generally radially outward direction proximal the introducer 30; it will be understood that this representation is provided to better illustrate the wires 52 and the stylet 26 in the view. Preferably, the insulated wires 52 are maintained as a controlled grouping during the procedure.

Figure 6C:
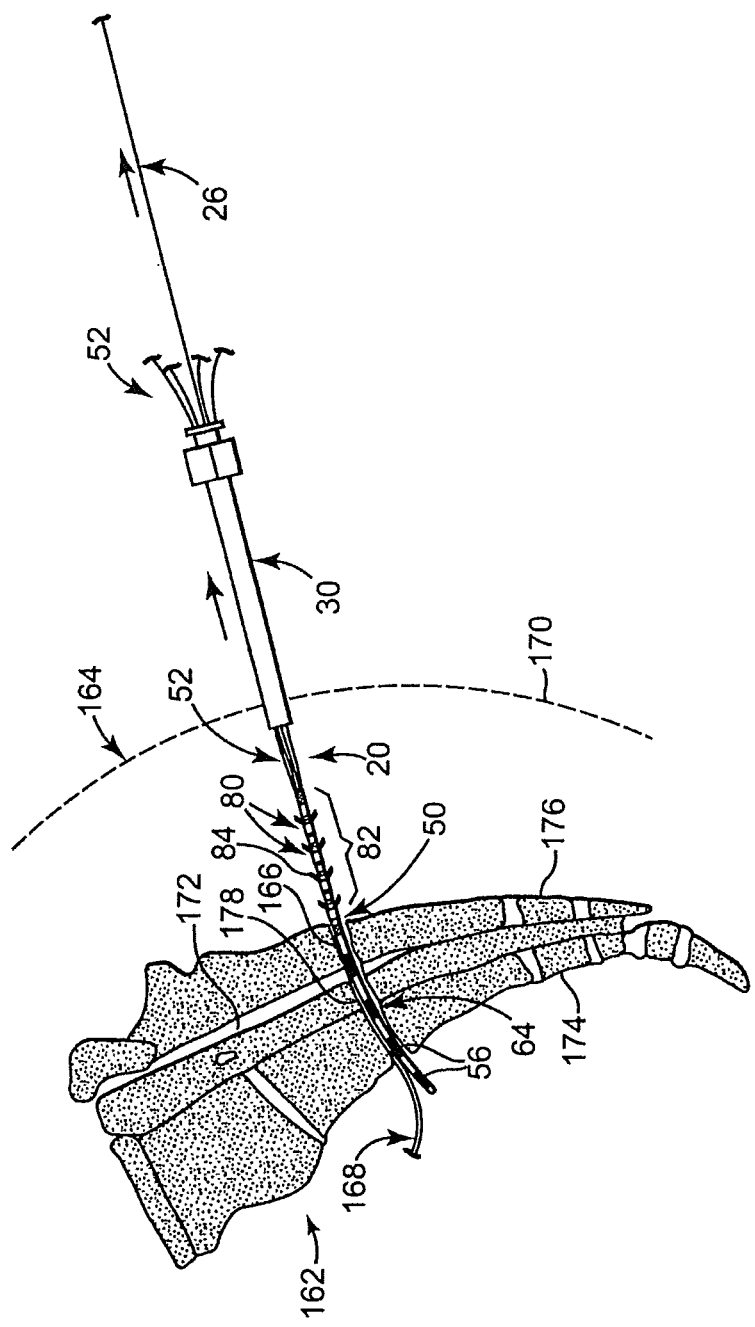

At step 186, the introducer 30 is retracted proximally from the lead 20 as shown in FIG. 6C, for example after electrical testing to establish optimal positioning of the stimulating electrode array 64 relative to the stimulation site 178. In connection with one embodiment in which the lead 20 includes the anchoring device(s) 80 in the form of tine assemblies, with proximal retraction of the introducer 30, the tines 84 are released/deployed as shown in FIG. 6C. When each of the tines 84 are released in subcutaneous tissue, they bear against the tissue and inhibit proximal retraction of the lead body 50 though the subcutaneous tissue if traction is applied to the lead 20 since the tines 84 resist inversion in the proximal direction. Thus, the anchoring device(s) 80 serve to inhibit migration of the stimulating electrodes 56. Alternative embodiments of the anchoring device(s) 80 may or may not operate or function in a similar manner. Regardless, the stylet 26 is also removed with removal of the introducer 30.

Figure 6D:
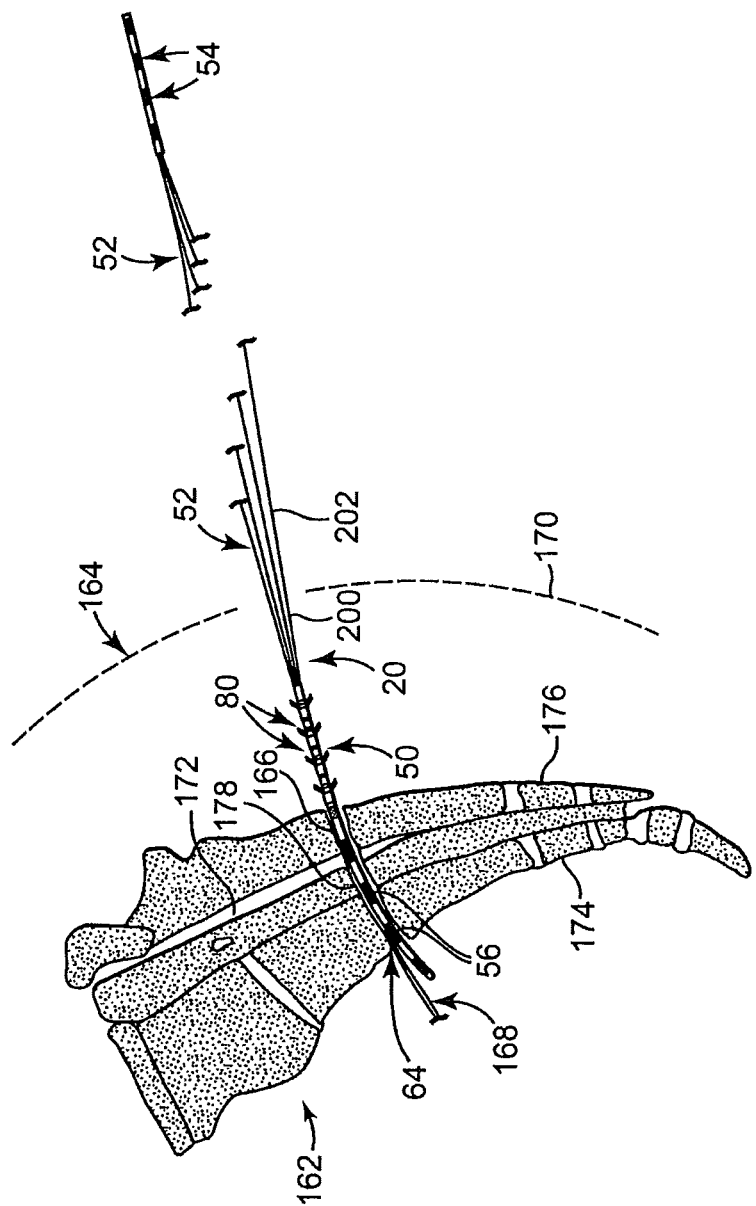

Upon removal of the introducer 30 (as well as the stylet 26), the insulated wires 52 extend proximally from the proximal end of the lead body 50 and through the skin incision as shown in FIG. 6D. Relative to this orientation, then, the insulated wires 52 each are effectively defined by a subcutaneous region 200 (i.e., beneath the patient's skin 170) and an external region 202. The external regions 202 of the insulated wires 50 are, at step 188, moved as desired by the clinician to a location external the patient for connection to the power source 22 (FIG. 1). For example, the external regions 202 of the wires can be curved, bent, etc., along the patient's exterior body/skin to a desired location. In connection with step 188, and unlike conventional techniques, methods in accordance with the present invention are characterized by the clinician not performing a subcutaneous tunneling procedure (for example the subcutaneous tunneling procedure commonly performed with permanent implantation of a sacral nerve electrical stimulation system) to subcutaneously locate the wires 52 (or any other cabling that might be associated with the lead 20). Further, methods in accordance with principles of the present invention are characterized by the clinician not being required to perform an additional step of connecting the lead body 50/stimulating electrodes 56 to a percutaneous cable extension upon implanting of the lead body 50.

Following, simultaneously with, or prior to step 188, at step 190, the insulated wires 52, or at least portions thereof, are individually sealed to the patient's skin 170 at the initial incision to block wound infection. This can be accomplished in a variety of known fashions, such as by suturing, surgical glue, etc., and serves to prevent infection.

The electrical conductor elements 54 of the lead 20 can then be electrically coupled to the power source 22 (FIG. 1) at step 192, followed by providing electrical energy from the power source 22 to the stimulating electrodes 56 (via the insulated wires 52) at step 194 as part of an bodily tissue electrical stimulation procedure (e.g., as part an a peripheral sacral nerve stimulation evaluation test in which the sacral nerve is periodically and/or continuously electrically stimulated over the course of a test period (e.g., typically 3-7 days) to evaluate whether the patient is an appropriate candidate for a permanently implanted sacral nerve stimulation system). In one embodiment, the power source 22 is a pulse generator (e.g., a Model 3625 InterStim® Test Stimulator available from Medtronic, Inc., of Minneapolis, Minn.). Regardless, the power source 22 is maintained external the patient's skin. Further, the stimulating electrode array 64 can operate in a bipolar mode in delivering the stimulating energy to the sacral nerve(s) 168.

Following completion of the stimulation procedure (e.g., at the end of the stimulation evaluation period), the lead body 50 is removed from the stimulation site 178 at step 194. In one embodiment, the lead body 50 can be explanted by applying a gentle pulling or tugging force on to the external region 202 of one or more of the wires 52, which in turn translate this force on to the lead body 50. Alternatively or in addition, a gentle pulling or tugging force can be applied to the tether 130 (FIG. 1) (where provided) external the patient; the tether 130 translates this force on to the lead body 50 to effectuate removal of the lead body 50 from the patient.

Unlike conventional PNE-type leads commonly used as temporarily implanted bodily tissue electrical stimulation devices, the lead 20 in accordance with principles of the present invention provides a more rigid resistance to migration via the anchoring device(s) 80 (for example, where the anchoring device(s) 80 are provided in the form of tine assemblies that otherwise interface with subcutaneous tissue) along with bipolar operation. Conversely, unlike convention permanent or chronic leads, the lead 20 in accordance with principles of the present invention does not require a subcutaneous tunneling procedure to effectuate final implantation, permits sealing at the skin surface to block wound infection, and does not require that a separate percutaneously cabling be connected to the lead body. As a result, the lead 20 in accordance with principles of the present invention can be temporarily implanted on a relatively expedited basis (e.g., performed in an office setting rather than requiring an operating room) and better resists migration.

Figure 7:
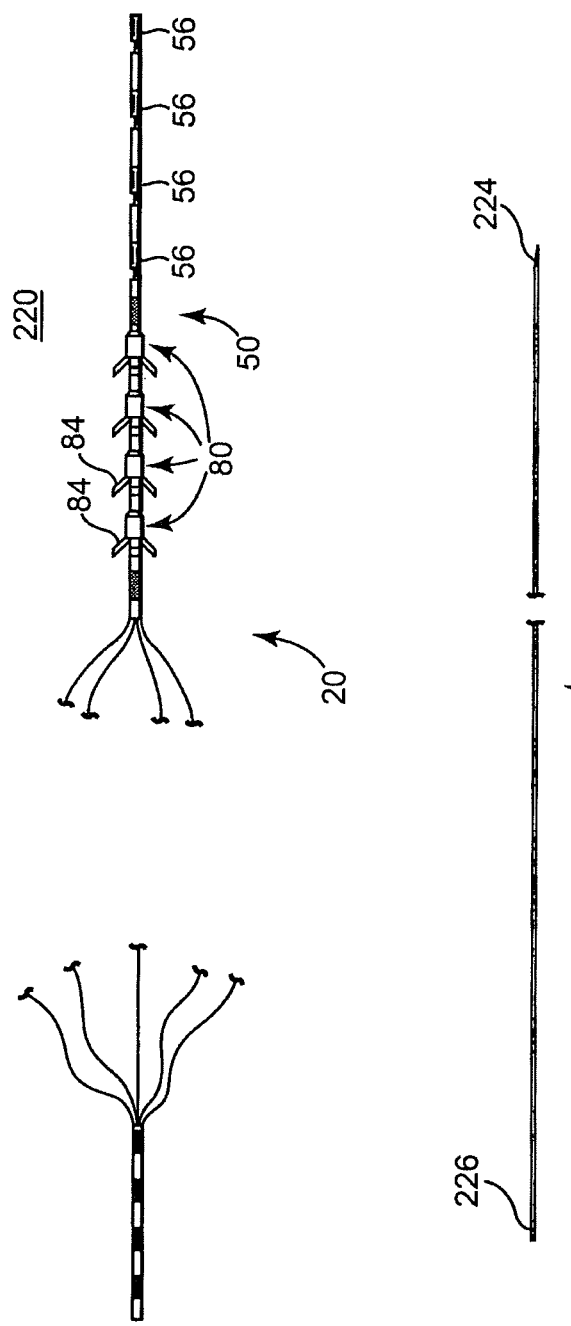
FIG. 7 is a simplified plan view an alternative embodiment system for providing medical electrical stimulation to a patient in accordance with principles of the present invention.

The lead 20 in accordance with the present invention can be implanted in a variety of different fashions differing to certain extents from the one embodiment methodology described above, and can thus be provided as part of a system with one or more components differing from the system 24 of FIG. 1. For example, an alternative embodiment system 220 in accordance with principles of the present invention is shown in simplified form in FIG. 7, and includes the lead 20 as described above, along with a directional guide wire/stylet 222. The guide wire 222 is akin to the stylet 26 of FIG. 1, and is sized to be slidably received with the lumen 70 (FIG. 2) defined by the lead body 50. With the one embodiment of FIG. 7, however, the guide wire 222 has a needle-like distal tip 224 and is adapted to serve as a probe. For example, the guide wire 222 can be formed of an electrically conductive metal covered by (except at the distal tip 224 and a proximal end 226) an electrically non-conductive or insulating material (e.g., a parylene coating). With this arrangement, the guide wire 222 can be used to initially percutaneously locate the desired stimulation site (thus replacing the needle described above), with the lead 20/lead body 50 being delivered to the stimulation site over the guide wire 222. It will be recognized that with this one alternative approach, where the anchoring device(s) 80 of the lead 20 are tine assemblies, the tines 84 are preferable configured to exhibit sufficient flexibility to permit ready advancement through the incision/wound formed through the patient's skin and/or a pusher component (not shown) can be further included to facilitate distal delivery of the lead 20 over the guide wire 222. Alternatively, the system 220 can further include an introducer (not shown but akin, in some embodiments, to the introducer 30 of FIG. 1) that forces the tine assemblies 80 to a folded state as part of the percutaneous insertion over the guide wire 222. Along these same line, the introducer can define the channel through which the guide wire 222 is slidably received.

Although the present invention has been described with reference to preferred embodiments, workers skilled in the art will recognize that changes can be made in form and detail without departing from the spirit and scope of the present invention.

What is claimed is:

1. A system for applying an electrical stimulation energy to bodily tissue of a patient from a power source located external the patient, the system comprising:
    a lead defined by a distal section, an intermediate section, and a proximal section, the lead including:
        a lead body at the distal section and including a plurality of stimulating electrodes arranged in an electrode array, and at least one anchoring device,
        a plurality of wire lead conductors wound to define a lumen of the lead body and each wire lead conductor being electrically coupled to a respective one of the stimulating electrodes; and
        a plurality of insulated conductor wires electrically isolated from one another and each having an intermediate segment and a proximal segment terminating at a proximal end, wherein each of the insulated conductor wires is electrically coupled to a respective one of the wire lead conductors and the intermediate segments extend proximal the lead body and are characterized as having a non-coiled configuration and wherein individual ones of the plurality of insulated wires are not exteriorly enclosed along the intermediate segment apart from a component separate from the lead; and
    a stylet slidably disposed within the lumen of the lead body and extending proximally therefrom.

2. The system of claim 1, wherein the stylet defines a distal portion, an intermediate portion, and a proximal portion, the intermediate portion being selectively associated with the intermediate segments of the insulated wires upon final assembly of the distal portion of the stylet within the lead body lumen.

3. The system of claim 2, wherein the intermediate portion of the stylet is not directly connected to the intermediate segments of the insulated wires.

4. The system of claim 2, wherein each of the intermediate segments characterized as having the non-coiled configuration does not individually form an internal passage, wherein the intermediate segments of the insulated wires are wrapped about the intermediate portion of the stylet.

5. The system of claim 4, wherein the intermediate segments of the insulated conductor wires are freely movable upon removal of the stylet.

6. The system of claim 1, further comprising:
    a connector assembly maintaining a connector array electrically coupled to the proximal segments of the plurality of insulated conductor wires and a proximal portion of the stylet.

7. The system of claim 6, further comprising:
    an introducer including a sheath defining a lumen sized to coaxially receive the lead body;
    wherein the connector assembly and the introducer assembly are configured to be releasably mounted to one another.

8. The system of claim 1, wherein the lead body lumen is open at a distal end of the lead body, and further wherein the stylet is a directional guide wire having an electrode tip that is distally extendible through the lead body lumen.

9. The system of claim 8, wherein the electrode tip is a needle tip.

10. The system of claim 1, wherein the lead includes at least two of the stimulating electrodes and a corresponding number of the insulated wires.

11. The system of claim 1, further comprising a tubular sheath further defining the lumen of the lead body.

12. The system of claim 1, wherein the plurality of wire lead conductors integrally define distal segments of the plurality of insulated wire conductors.

13. The system of claim 1, wherein the intermediate segments of the insulated conductor wires are freely movable relative to one another.

14. A system for applying an electrical stimulation energy to bodily tissue of a patient from a power source located external the patient, the system comprising:
    a lead defined by a distal section, an intermediate section, and a proximal section, the lead including:
        a lead body at the distal section and including a plurality of stimulating electrodes arranged in an electrode array, and at least one anchoring device,
        a plurality of wire lead conductors wound to define a lumen of the lead body and each wire lead conductor being electrically coupled to a respective one of the stimulating electrodes; and
        a plurality of insulated conductor wires electrically isolated from one another and each having an intermediate segment and a proximal segment terminating at a proximal end, wherein each of the insulated conductor wires is electrically coupled to a respective one of the wire lead conductors and the intermediate segments extend proximal the lead body and are characterized as having a non-coiled configuration and do not individually form an internal passage; and
    a stylet slidably disposed within the lumen of the lead body and extending proximally therefrom and wherein the stylet defines a distal portion, an intermediate portion, and a proximal portion, the intermediate portion being selectively associated with the intermediate segments of the insulated wires upon final assembly of the distal portion of the stylet within the lead body lumen, and
    wherein the intermediate segments of the insulated wires are wrapped about the intermediate portion of the stylet and are freely movable upon removal of the sylet.

* * * * *